United States Patent [19]
Hill et al.

[11] Patent Number: 6,127,135
[45] Date of Patent: Oct. 3, 2000

[54] METHODS OF OBTAINING COMPOSITIONS ENRICHED FOR HEMATOPOIETIC STEM CELLS, ANTIBODIES FOR USE THEREIN, COMPOSITIONS DERIVED THEREFROM AND METHODS OF USE THEREOF

[76] Inventors: Beth Louise Hill, 780 Bond Way; Elen Rozler, 255 Rengstorff Ave., Apt. 130, both of Mountain View, Calif. 94040; Benjamin P. Chen, 2711 Parkside Dr., Fremont, Calif. 94536

[21] Appl. No.: 09/085,193

[22] Filed: May 27, 1998

Related U.S. Application Data

[62] Division of application No. 08/806,380, Feb. 27, 1997, Pat. No. 5,814,440, which is a continuation of application No. 08/474,792, Jun. 7, 1995, abandoned.

[51] Int. Cl.[7] .................. G01N 33/53; G01N 33/536; C07K 16/28; C07K 16/18
[52] U.S. Cl. .................. 435/7.24; 435/7.1; 435/7.2; 435/7.21; 435/343; 436/501; 436/536; 530/388.7; 530/389.6
[58] Field of Search .................. 435/7.1, 343, 7.2, 435/7.24, 7.21; 436/501, 536; 530/388.7, 389.6

[56] References Cited

U.S. PATENT DOCUMENTS

| | | | |
|---|---|---|---|
| 4,714,680 | 12/1987 | Civin | 435/347 |
| 5,061,620 | 10/1991 | Tsukamoto | 435/7.21 |
| 5,147,784 | 9/1992 | Peault | 435/7.24 |

FOREIGN PATENT DOCUMENTS

| | | |
|---|---|---|
| 341966 | 11/1989 | European Pat. Off. . |
| 95/03693 | 2/1995 | WIPO . |
| 95/05843 | 3/1995 | WIPO . |

OTHER PUBLICATIONS

Baum et al., *Proc. Nat'l. Acad. Science USA,* 1992, 89:2804–2808.
Chaudhary and Roninson, *Cell,* 1991, 66:85–94.
Spangrude et al., *Science,* 1998, 241:58–62.
Smith et al., *Proc. Nat'l. Acad. Sci., USA* 88:2788–2792.
Uchida, *Ph.D. Thesis,* 1992, Stanford University.
Issaragrishi et al., *New England Journal of Medicine,* 1995, 332:367–369.
Whitlock and Witte, *Proc. Natl., Acad. Sci. USA,* (1982), 79:3608–3612.
Whitlock et al., *Cell,* 1987, 48:1009–1021.
Kyoizumi et al., *Blood,* 1992, 79:1704.
Chen et al., *Blood,* 1994, 84:2497.
Galfre et al., *Nature,* 1997, 266:550–552.
Galy et al., *Blood,* 1994, 84:104–110.
Haugland, R. P., *Molecular Probes: Handbook of Fluorescent Probes and Research Chemicals,* 1992–1994, Table of contents.
Brandt et al., *Blood,* 1992, 79:634–641.
Zittoun et al., *N. Engl. J. Med.,* , 1995, 332:217–223.
Hill et al., *Blood,* 1994, 84:1729.
Helbig et al., *J. Clin. Micro.,* 31:3211–3215.

*Primary Examiner*—Ronald B. Schwadron
*Attorney, Agent, or Firm*—Melissa A. Shaw; Lynn Marcus-Wyner

[57] ABSTRACT

This invention provides a novel antibody, designated the αEM10 antibody. Also provided are methods of determining hematopoietic stem cell content. The methods employ using antibodies (αEM10) specific for a unique cell marker (EM10) that is expressed on stem cells.

6 Claims, 10 Drawing Sheets

ISOTYPE CONTROL

Thy-1

Thy-1

METHODS OF OBTAINING COMPOSITIONS ENRICHED FOR HEMATOPOIETIC STEM CELLS, ANTIBODIES FOR USE THEREIN, COMPOSITIONS DERIVED THEREFROM AND METHODS OF USE THEREOF

This application is a divisional application of application Ser. No. 08/806,380, filed Feb. 27, 1997, now U.S. Pat. No. 5,814,440, which is a continuation application of application Ser. No. 08/474,792, filed Jun. 7, 1995, now abandoned.

INTRODUCTION

1. Technical Field

The field of this invention is the isolation of a population of cells enriched for human hematopoietic stem cells.

2. Background

Mammalian hematopoietic cells provide a diverse range of physiological activities. These cells are divided into lymphoid, myeloid and erythroid lineages. The lymphoid lineage, comprising B cells and T cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies, provides protection against neoplastic cells, scavenges foreign materials, produces platelets, and the like. The erythroid lineage provides the red blood cells, which act as oxygen carriers.

All publications cited herein are hereby incorporated herein by reference in their entirety.

Despite the diversity of the nature, morphology, characteristics and function of hematopoietic cells, it is presently believed that these cells are derived from a single precursor cell population, termed "stem cells." Stem cells are capable of self-regeneration and can become lineage committed progenitors which are dedicated to differentiation and expansion into a specific lineage. As used herein, "stem cells" refers to hematopoietic cells and not stem cells of other cell types.

A pluripotent stem cell can be defined as follows: (1) gives rise to progeny in all defined hematolymphoid lineages; and (2) limiting numbers of cells are capable of fully reconstituting a seriously immuno-compromised host in all blood cell types and their progenitors, including the pluripotent hematopoietic stem cell, by self-renewal.

A highly purified population of stem cells is necessary for a variety of in vitro experiments and in vivo indications. For instance, a purified population of stem cells will allow for identification of growth factors associated with their self-regeneration. In addition, there can be as yet undiscovered growth factors associated with: (1) the early steps of dedication of the stem cell to a particular lineage; (2) the prevention of such dedication; and (3) the negative control of stem cell proliferation.

Stem cells find use in: (1) regenerating the hematopoietic system of a host deficient in any class of hematopoietic cells; (2) a host that is diseased and can be treated by removal of bone marrow, isolation of stem cells and treatment with drugs or irradiation prior to re-engraftment of stem cells; (3) producing various hematopoietic cells; (4) detecting and evaluating growth factors relevant to stem cell self-regeneration; and (5) the development of hematopoietic cell lineages and assaying for factors associated with hematopoietic development.

Stem cells are important targets for gene therapy, where the inserted genes promote the health of the individual into whom the stem cells are transplanted. In addition, the ability to isolate stem cells can serve in the treatment of lymphomas and leukemias, as well as other neoplastic conditions where the stem cells are purified from tumor cells in the bone marrow or peripheral blood, and reinfused into a patient after myelosuppressive or myeloablative chemotherapy. Thus, there have been world-wide efforts toward isolating stem cells in substantially pure or pure form.

Stem cells constitute only a small percentage of the total number of hematopoietic cells. Hematopoietic cells are identifiable by the presence of a variety of cell surface "markers." Such markers can be either specific to a particular lineage or progenitor cell or be present on more than one cell type. Currently, it is not known how many of the markers associated with differentiated cells are also present on stem cells. One marker, which was previously indicated as present solely on stem cells, CD34, is also found on a significant number of lineage committed progenitors. U.S. Pat. No. 4,714,680 describes a population of cells expressing the CD34 marker.

In view of the small proportion of the total number of cells in the bone marrow or peripheral blood which are stem cells, the uncertainty of the markers associated with the stem cell as distinct from more differentiated cells, and the general difficulty in assaying for stem cells biologically, the identification and purification of stem cells has been elusive. Characterizations and isolation of stem cells are report-d in: Baum et al. (1992) Proc. Natl. Acad. Sci. USA 9:2804–2808; and Tsukamoto et al. U.S. Pat. No. 5,061,620.

Decreased rhodamine 123 (rho123) staining of hematopoietic cells appears to correlate to stem cell potential. This so-called "rho$^{lo}$" marker is determined not by the initial dye accumulation but by an efflux process sensitive to P-glycoprotein (P-gp) inhibitors. Retention of several P-gp-transported fluorescent dyes, including rho123, in human bone marrow cells was inversely correlated with the expression of P-gp. Bone marrow cells expressing physical and antigenic characteristics of pluripotent stem cells show high levels of P-gp expression and fluorescent dye efflux. Fractions of human bone marrow cells isolated on the basis of either increased rho123 efflux or P-gp expression contain practically all the primitive progenitor cells of human bone marrow, including long-term culture-initiating cells (LTC-IC). Chaudhary and Roninson (1991) Cell 66:85–94.

Recently, the mouse stem cell has been obtained in at least highly concentrated, if not purified form, where fewer than about 30 cells obtained from bone marrow were able to reconstitute all of the lineages of the hematopoietic system of a lethally irradiated mouse. Each assayed cell is multipotent for all hematopoietic lineages, while self-renewal is variable amongst these cells. Spangrude et al. (1988) Science 241:58–62; Smith et al. (1991) Proc. Natl. Acad. Sci. USA 88:2788–2792; Uchiaa (1992) Ph.D. Thesis Stanford U.; and see also, EPA 89 304651.6 and the references cited therein which describe the isolation of mouse stem cells.

SUMMARY OF THE INVENTION

Methods are provided to obtain compositions enriched for hematopoietic stem cells. The methods employ a separation regimen utilizing antibodies (αEM10) specific for a unique cell surface marker (EM10) that is expressed on stem and progenitor cells (EM10$^+$ cells), while being less accessible or absent on more mature cells.

Positive selection of stem cells with antibodies that recognize EM10 can be used in combination with selection for cells expressing other stem cell markers and/or negative selection with lineage-specific (LIN⁻) markers. Enriched populations of cells derived from these methods are also provided.

BRIEF DESCRIPTION OF THE DRAWINGS

FIGS. 3A–F depicts FACS analyses of various bone marrow (BM) populations.

FIGS. 6A and 6C were stained with and antibodies to EM10 and Thy-1 (FIG. 6A) or CD34 (FIG. 6B). FIGS. 6C and 6D were stained with antibody to CD34 and antibodies to EM10 (FIG. 6C) or isotype control (FIG. 6D).

FIGS. 7A and B depicts graphs of the long term cobblestone area forming cells (CAFC) frequency of various cell populations in co-culture with a murine stromal cell line. In FIGS. 7A and 7B the closed diamonds represent CD34⁺ cells, the closed squares represent CD34⁺ EM10⁺ cells and the closed triangles represent CD34⁺ EM10⁻ cells.

DEPOSIT INFORMATION

The hybridoma producing antibody SM27-1045 was deposited with the American Type Culture Collection (ATCC) 10801 University Boulevard, Manassas, Va., 20110-2209, USA on Jun. 2, 1995 under the provisions of the Budapest Treaty of the International Recognition of the Deposit of Microorganisms for the Purpose of Patent Procedure under Accession No. HB11917.

DESCRIPTION OF THE SPECIFIC EMBODIMENTS

The present invention provides methods for isolating a population of hematopoietic cells highly enriched for stem cells.

Figure 1A:
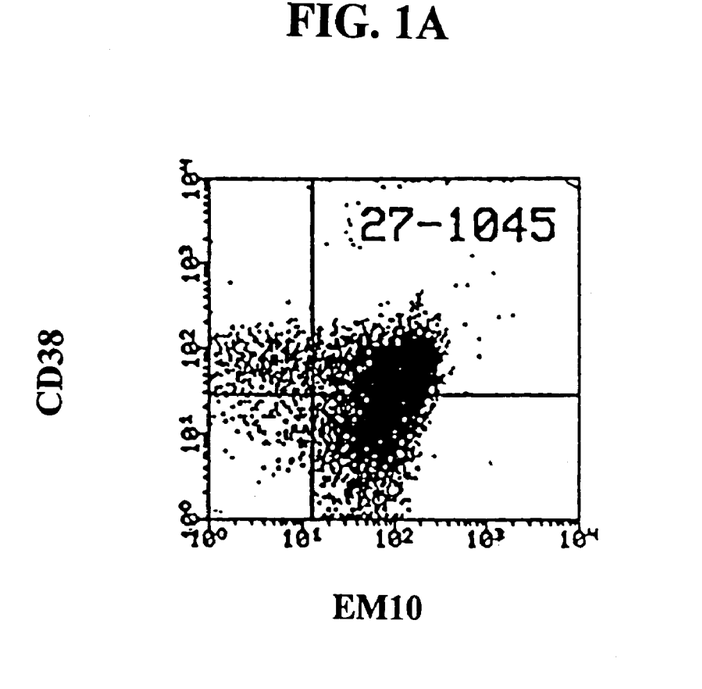
FIGS. 1A and B depicts 3-color FACS analyses of CD34⁺ cells stained with antibodies to CD38 and αEM10 (FIG. 1A) or IgM isotype control (FIG. 1B).
Figure 1B:
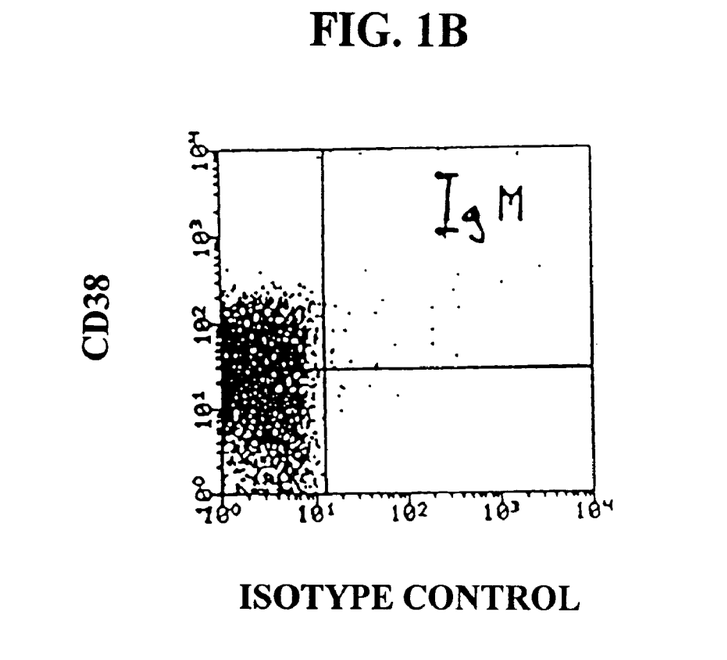
Figure 2A:
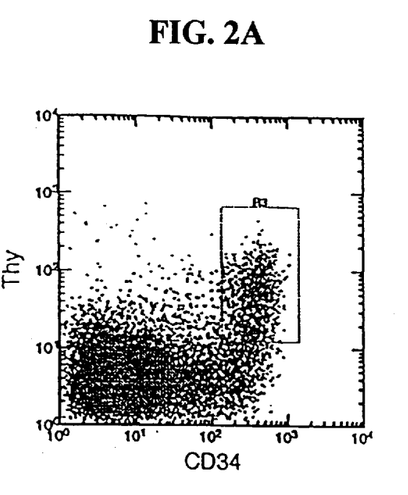
FIGS. 2A–C depicts five color FACS analyses of CD34⁺ Thy-1⁺ gated cells (FIG. 2A) stained with rhodamine 123 and αEM10 (SM27-1045) (FIG. 2B) or IgM isotype control (FIG. 2C).
Figure 2B:
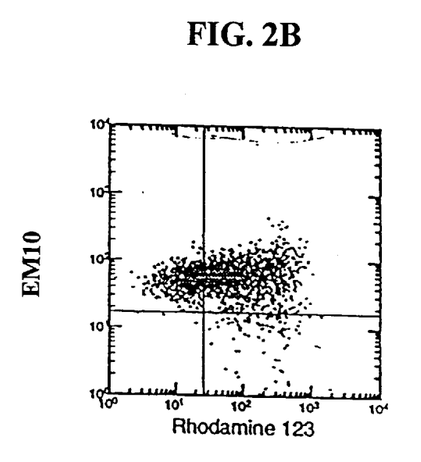
Figure 2C:
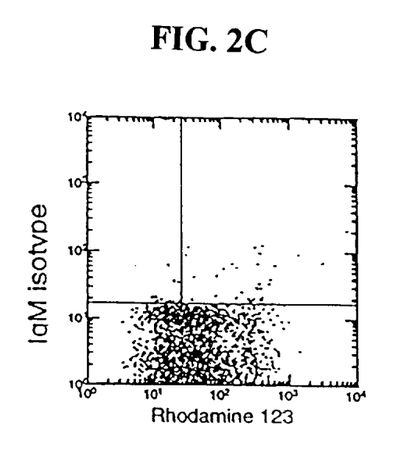
Figure 3A:
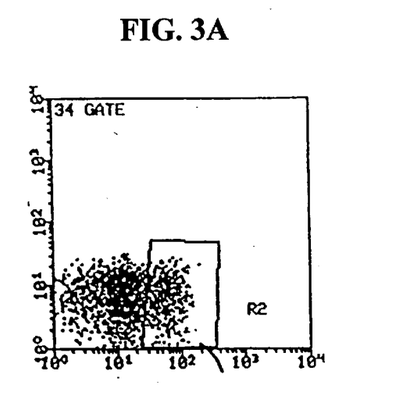
FIG. 3A depicts FACS analysis of cells sorted with antibodies to CD34.
Figure 3B:
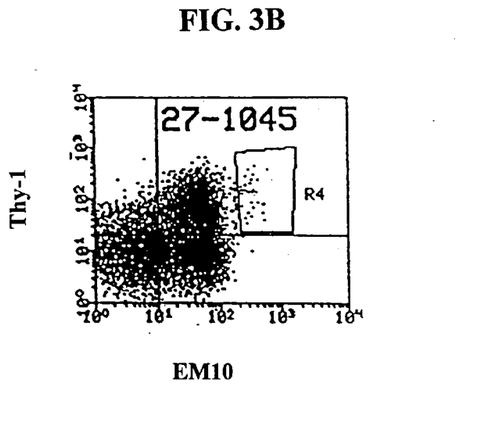
FIG. 3B depicts anti-Thy-1 and αEM10 (SM27-1045) FACS analysis of an electronically gated population of CD34⁺ cells (R2) depicted in FIG. 3A.
Figure 3C:
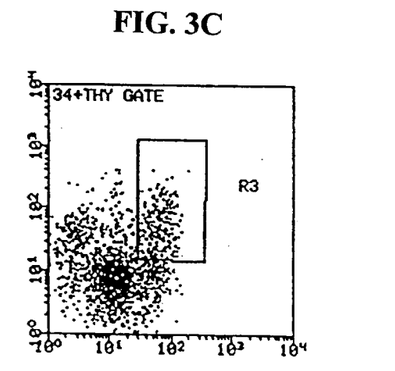
FIG. 3C depicts FACS analysis of cells stained with antibodies to CD34 and Thy-1 to obtain CD34⁺Thy-1⁺ cells (R3).
Figure 3D:
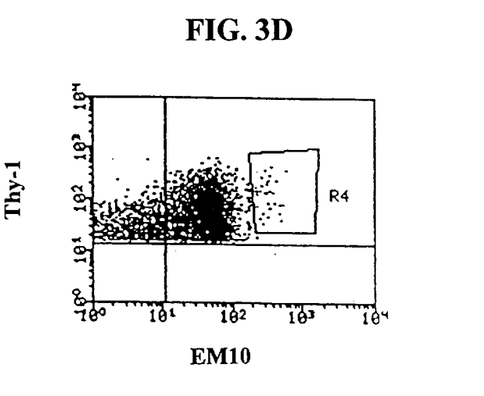
FIG. 3D depicts anti-Thy-1 and αEM10 FACS analysis of the electronically gated population of CD34⁺ Thy-1⁺ cells (R3) of FIG. 3C.
Figure 3E:
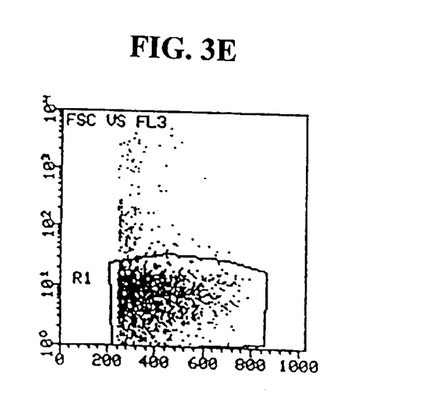
FIG. 3E depicts FACS analysis of all viable BM cells sorted by forward scatter (FSC) and propidium iodide staining (R1).
Figure 3F:
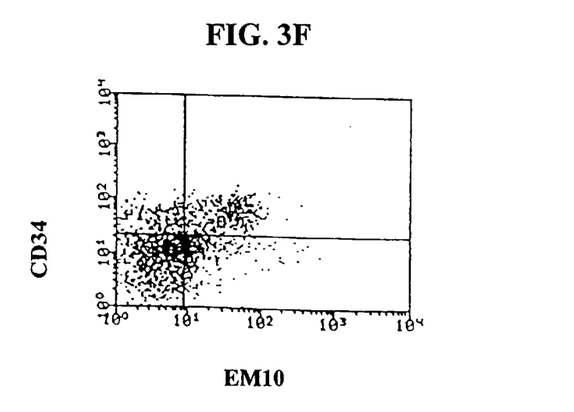
FIG. 3F depicts anti-CD34 and αEM10 (SM27-1045) staining of the electronically gated population of the cells (R1) of FIG. 3E.
Figure 4A:
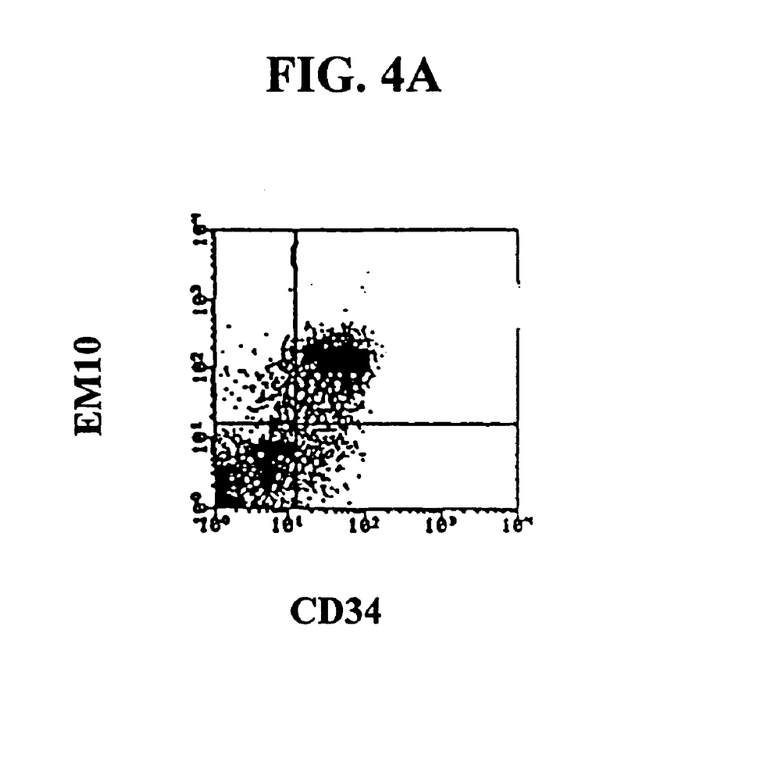
FIGS. 4A and B depicts 2-color FACS analyses of cells stained with antibodies to CD34 and EM10 (FIG. 4A) or IgM isotype control antibody (FIG. 4B).
Figure 4B:
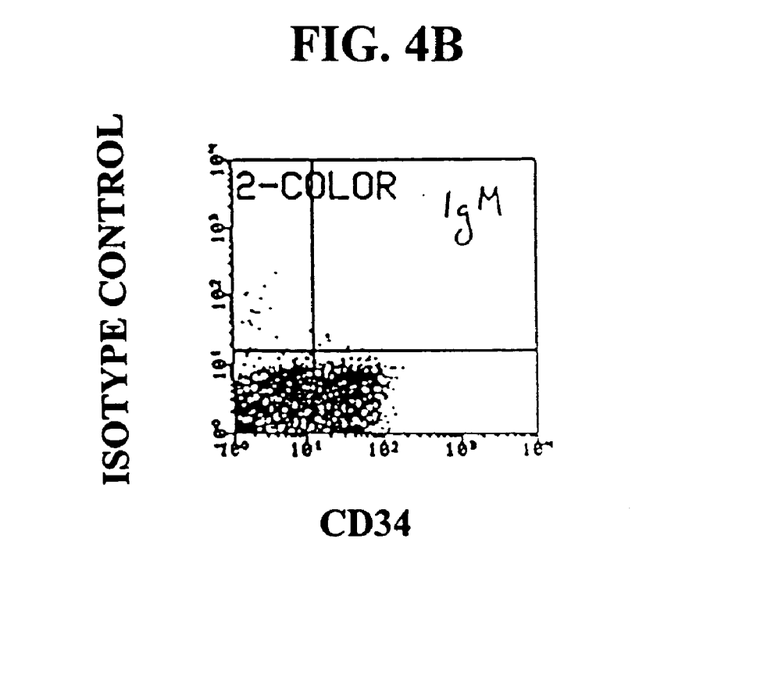

It has now been found that the cell surface marker ("EM10") recognized by antibodies specific for EM10 ("αEM10") is expressed on hematopoietic stem cells. αEM10 subdivide the CD34⁺ cell population into approximately equal subpopulations, with the stem cell activity found predominantly in the EM10⁺ subpopulation. As described in detail in the examples section herein, αEM10 has the following characteristics. αEM10 binds approximately 60% of CD34⁺ cells and 1–2% of mononuclear cells on average. αEM10 binds to a substantial subset of CD34⁺ CD38⁻ cells. FIGS. 1A and B. αEM10 binds a substantial subset of all CD34⁺Thy-1⁺ (both rho123$^{lo}$ and rho132$^{hi}$ subsets). FIGS. 2A–C. αEM10 binds significant numbers of CD34⁺Thy-1⁻ cells. FIGS. 3A–F. αEM10 does not bind significant numbers of CD34⁻ cells. FIGS. 4A and B. Exemplary of an αEM10 antibody is the monoclonal antibody SM27-1045 described in the examples herein.

Thus, αEM10 can be used in place of antibodies to other stem cell markers e.g. CD34, to purify the majority of progenitor cells and pluripotent stem cells from heterogeneous populations of hematopoietic cells. αEM10 binds to a larger subset of CD34⁺ cells than do mAbs to Thy-1. As described more fully in the examples section, EM10 defines a population of cells which is enriched in CFU-GM, in addition to the CAFC activity, which provides a desirable bone marrow graft composition. Further, based on SCID-hu thymus data, the EM10⁺CD34⁺ cells may include T cell progenitors activity.

The present invention thus encompasses methods of obtaining a composition substantially enriched in stem cells. The methods involve combining a mixture of hematopoietic cells with an antibody that recognizes and binds to EM10 under conditions which allow the antibody to bind to EM10 and separating the cells recognized by the antibody to obtain a population substantially enriched in EM10⁺ cells. The methods can be used as a diagnostic assay for the number of stem cells in a sample of hematopoietic cells. The cells and antibody are combined under conditions sufficient to allow specific binding of the antibody to EM10 and the EM10⁺ cells are then quantitated. The EM10⁺ cells can be isolated or further purified.

The results presented herein show that the EM10⁺ population includes the CD34⁺Thy-1⁺ population of cells which have previously been shown to be primitive pluripotential hematopoietic progenitors. (FIGS. 2A–C) Thus, EM10 is expressed on the subset of CD34⁺ cells which contains virtually all primitive hematopoietic stem cells and αEM10 enables the purification of this subset of hematopoietic stem cells.

The methods can include further enrichment steps for cells by positive selection for other stem cell specific markers. Suitable positive stem cell markers include, but are not limited to, CD34⁺, Thy-1⁺, c-kit⁺. Preferably the EM10⁺ cells are human but can be derived from any suitable animal. By appropriate selection with particular factors and the development of bioassays which allow for self-regeneration of stem cells and screening of the stem cells as to their markers, a composition enriched for viable stem cells can be produced for a variety of purposes.

Preferably, the cells are subject to negative selection to remove those cells that express lineage specific markers and retain those cells which are lineage negative ("LIN⁻"). Methods of negative selection are known in the art. LIN⁻ cells generally refer to cells which lack markers associated with T cells (such as CD2, 3, 4 and 8), B cells (such as CD10, 19 and 20), myeloid cells (such as CD14, 15, 16 and 33), natural killer ("NK") cells (such as CD2, 16 and 56), RBC (such as glycophorin A), megakaryocytes (CD41), mast cells, eosinophils or basophils. The absence or low expression of such lineage specific markers is identified by the lack of binding of antibodies specific to the cell specific markers, useful in so-called "negative selection". Preferably the lineage specific markers include, but are not limited to, at least one of CD2, CD14, CD15, CD16, CD19, CD20, CD38, HLA-DR and CD71; more preferably, at least CD14 and CD15. A highly enriched composition can be obtained by selective isolation of cells that are $CD34^+EM10^+LIN^-$.

Table 1 summarizes probable phenotypes of stem cells in fetal, adult, and mobilized peripheral blood. In Table 1, myelomonocytic stands for myelomonocytic associated markers, NK stands for natural killer cells, FBM stands for fetal bone marrow, ABM stands for adult bone marrow, and AMPB stands for adult mobilized peripheral blood. As used herein, both infra, supra and in Table 1, the negative sign or superscript negative sign ($^-$) means that the level of the specified marker is undetectable above Ig isotype controls by fluorescent activated cell sorting (FACS) analysis, and includes cells with very low expression of the specified marker.

of the total cells present not having the marker can remain with the cell population to be retained. The particular technique employed will depend upon efficiency of separation, associated cytotoxicity, ease and speed of performance, and necessity for sophisticated equipment and/or technical skill.

Procedures for separation can include, but are not limited to, magnetic separation, using antibody-coated magnetic beads, affinity chromatography, cytotoxic agents joined to a monoclonal antibody or used in conjunction with a monoclonal antibody, including, but not limited to, complement and cytotoxins, and "panning" with antibody attached to a solid matrix, e.g., plate, elutriation or any other convenient technique.

The use of separation techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye Hoechst 33342).

Techniques providing accurate separation include, but are not limited to, FACS, which can have varying degrees of sophistication, e.g., a plurality of color channels, low angle and obtuse light scattering detecting channels, impedance channels, etc.

TABLE 1

Probable Stem Cell Phenotypes

| | NK and T cell markers | | | B cell markers | | | Myelomonocytic | | | Other | | | | | | P-gp |
|---|---|---|---|---|---|---|---|---|---|---|---|---|---|---|---|---|
| | CD2 | CD3 | CD8 | CD10 | CD19 | CD20 | CD14 | CD15 | CD16 | CD33 | CD34 | CD38 | HLA-DR | C-Kit | Thy | Rho | Activity |
| FBM | − | − | − | − | − | − | − | − | − | ? | + | − | + | + | + | lo | + |
| ABM | − | − | − | − | − | − | − | − | − | − | + | − | lo/− | + | + | lo | + |
| AMPB | − | − | − | − | − | − | − | − | − | lo/−? | + | ? | lo/− | ? | + | lo | + |

$EM10^+$ stem cells can be isolated from any known source of stem cells, including, but not limited to, bone marrow, both adult and fetal, mobilized peripheral blood (MPB) and umbilical cord blood. The use of umbilical cord blood is discussed, for instance, in Issaragrishi et al. (1995) N. Engl. J. Med. 332:367–369. Initially, bone marrow cells can be obtained from a source of bone marrow, including but not limited to, ilium (e.g. from the hip bone via the iliac crest), tibia, femora, spine, or other bone cavities. Other sources of stem cells include, but are not limited to, embryonic yolk sac, fetal liver, and fetal spleen.

For isolation of bone marrow, an appropriate solution can be used to flush the bone, including, but not limited to, salt solution, conveniently supplemented with fetal calf serum (FCS) or other naturally occurring factors, in conjunction with an acceptable buffer at low concentration, generally from about 5–25 mM. Convenient buffers include, but are not limited to, HEPES, phosphate buffers and lactate buffers. Otherwise bone marrow can be aspirated from the bone in accordance with conventional techniques.

Various techniques can be employed to separate the cells by initially removing cells of dedicated lineage. Monoclonal antibodies are particularly useful for identifying markers associated wish particular cell lineages and/or stages of differentiation. The antibodies can be attached to a solid support to allow for crude separation. The separation techniques employed should maximize the retention of viability of the fraction to be collected. Various techniques of different efficacy can be employed to obtain "relatively crude" separations. Such separations are where up to 10%, usually not more than about 5%, preferably not more than about 1%, In a first separation, typically starting with about $1 \times 10^{8-9}$, preferably at about $5 \times 10^{8-9}$ cells, αEM10 can be labeled with one fluorochrome, while the antibodies for the various dedicated lineages, can be conjugated to at least one different fluorochrome. While each of the lineages can be separated in a separate step, desirably the lineages are separated at the same time as one is positively selecting for EM10 and/or other stem cell markers. The cells can be selected against dead cells, by employing dyes associated with dead cells (including but not limited to, propidium iodide (PI)). Preferably, the cells are collected in a medium comprising 2% FCS.

The purified stem cells have low side scatter and low to medium forward scatter profiles by FACS analysis. Cytospin preparations show the enriched stem cells to have a size between mature lymphoid cells and mature granulocytes. Cells can be selected based on light-scatter properties as well as their expression of various cell surface antigens.

While it is believed that the particular order of separation is not critical to this invention, the order indicated is preferred. Preferably, cells are initially separated by a coarse separation, followed by a fine separation, with positive selection with αEM10.

Compositions having greater than 90%, usually greater than about 95% of $EM10^+$ cells can be achieved in this manner. The desired stem cells can be further enriched by selection for $LIN^-$ and/or $Thy-1^+$ and/or $rho^{lo}$, or combinations of these markers as listed in Table 2, and being able to provide for cell regeneration and development of members of all of the various hematopoietic lineages. Note that the blank spaces in Table 2 do not mean that the cells are negative for the specified marker; they simply mean the marker is not used.

TABLE 2

Possible Combinations of Selections for Stem Cell Populations

| EM10+ | CD34+ | Thy+ | LIN- | rho^lo |
|---|---|---|---|---|
| + | + | + | + | + |
| + | + | + | + |   |
| + | + | + |   |   |
| + | + |   |   |   |
| + | + |   |   | + |
| + |   | + |   | + |
| + |   | + | + | + |
| + |   |   | + | + |
| + |   |   | + |   |
|   | + | + | + |   |
|   | + | + | + | + |
|   |   | + | + | + |
| + |   |   | + | + |
|   |   |   | + | + |
|   |   | + |   | + |

By separating CD34+EM10+ cells from human hematopoietic sources, the long-term culture activity is enriched in the EM10+ fraction compared to EM10-. Moreover, the EM10+ cells will generate both B and myeloid cells in long-term cultures. In further enrichments of the EM10+ cells using antibodies to Thy-1 and/or any of the combinations specified in Table 2 and/or c-kit, the stem cell frequency can be further increased.

The cells obtained as described above can be used immediately or frozen at liquid nitrogen temperatures and stored for long periods of time, being thawed and capable of being reused. The cells will usually be stored in 10% DMSO, 50% fetal calf serum (FCS), 40% RPMI 1640 medium. Once thawed, the cells can be expanded by use of growth factors and/or stromal cells associated with stem cell proliferation and differentiation.

In another embodiment of the invention, a composition highly enriched in stem cells is provided. The results presented herein indicate that antibodies to EM10 recognize and bind with high specificity to a cell surface antigen found on human hematopoietic cells, and exposed to a high degree on stem cells. This specificity can be used to isolate and purify stem cells. Such a composition has utility in reconstituting hematopoietic systems and in studying various parameters of hematopoietic cells.

The compositions enriched for stem cells can be used in autologous hematopoietic engraftment, where the cells can be freed of neoplastic cells. Further, the use of autologous stem cells will avoid graft-versus-host disease. In addition, the cells can be modified by appropriate gene transfer, to correct genetic defects or provide genetic capabilities naturally lacking in the stem cells or their progeny, either as to the individual or as to hematopoietic cells generally. In addition, the stem cell composition can be used to isolate and define factors associated with their regeneration and differentiation.

The cells generated from EM10+ cells and obtained from these cultures give rise to B cells, T cells, erythroid cells and myelomonocytic cells in the in vivo assays described below. In vitro analyses for hematopoietic progenitor cells have also been reported by Whitlock and Witte (1982) Proc. Natl. Acad. Sci. USA 79:3608–3612; and Whitlock et al. (1987) Cell 48:1009–1021.

In vivo demonstration of sustained hematopoietic ability of the various cell populations can be accomplished by the detection of continued myeloid, erythroid and B-lymphoid cell production in the SCID-hu bone model. Kyoizumi et al. (1992) Blood 79:1704; Chen et al. (1994) Blood 84:2497. To analyze this potential, one can isolate human fetal bone and transfer a longitudinally sliced portion of this bone into the mammary fat pad of a scid/scid animal: the bone cavity is depleted of endogenous progenitor cells by whole body irradiation of the mouse host prior to injection of the test donor population. The HLA of the population which is injected is mismatched with the HLA of the recipient bone cells.

To demonstrate differentiation to T cells, fetal thymus is isolated and cultured from 4–7 days at about 25° C., so as to deplete substantially the lymphoid population. The cells to be tested for T cell activity are then microinjected into the thymus tissue, where the HLA of the population which is injected is mismatched with the HLA of the thymus cells. The thymus tissue can then be transplanted into a scid/scid mouse as described in U.S. Pat. No. 5,147,784, particularly transplanting under the kidney capsule. Specifically, a sorted population of EM10+ cells can be microinjected into HLA mismatched thymus fragments. After 6–10 weeks, assays of the thymus fragments injected with EM10+ cells can be performed and assessed for donor derived T cells.

The cell compositions can find use in a variety of ways. They can be used to fully reconstitute an immunocompromised host such as an irradiated host and/or a host subject to chemotherapy; or as a source of cells for specific lineages, by providing for their maturation, proliferation and differentiation into one or more selected lineages by employing a variety of factors, including, but not limited to, erythropoietin, colony stimulating factors, e.g., GM-CSF, G-CSF, or M-CSF, interleukins, e.g., IL-1, -2, -3, -4, -5, -6, -7, -8, etc., or the like, or stromal cells associated with the stem cells becoming committed to a particular lineage, or with their proliferation, maturation and differentiation.

The EM10+ cells can also be used in the isolation and evaluation of factors associated with the differentiation and maturation of hematopoietic cells. Thus, the invention encompasses the use of EM10+ cells in assays to determine the activity of media, such as conditioned media, or to evaluate fluids for cell growth activity, involvement with dedication of particular lineages, or the like.

The EM10+ cells can be used for the treatment of genetic diseases. Thus, the invention encompasses treatment of genetic diseases associated with hematopoietic cells by genetic modification of autologous or allogeneic stem cells to correct the genetic defect. For example, diseases including, but not limited to, β-thalassemia, sickle cell anemia, adenosine deaminase deficiency, recombinase deficiency, recombinase regulatory gene deficiency, etc. can be corrected by introduction of a wild-type gene into the EM10+ cells, either by homologous or random recombination. Other indications of gene therapy are introduction of drug resistance genes to enable normal stem cells to have an advantage and be subject to selective pressure during chemotherapy. Suitable drug resistance genes include, but are not limited to, the gene encoding the multidrug resistance (MDR) protein.

Diseases other than those associated with hematopoietic cells can also be treated by genetic modification, where the disease is related to the lack of a particular secreted product including, but not limited to, hormones, enzymes, interferons, growth factors, or the like. By employing an appropriate regulatory initiation region, inducible production of the deficient protein can be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic diseases.

In another embodiment, the invention encompasses antibodies which specifically recognize the cell surface marker having the epitope recognized by SM27-1045. As used herein, the term "αEM10" encompasses any antibody or fragment thereof, either native or recombinant, synthetic or naturally-derived, which retains sufficient specificity to bind specifically to the cell surface marker having the epitope recognized by SM27-1045. As used herein, the terms "antibody" or "antibodies" include the entire antibody and antibody fragments containing functional portions thereof. The term "antibody" includes any monospecific or bispecific compound comprised of a sufficient portion of the light chain variable region and/or the heavy chain variable region to effect binding to the epitope to which the whole antibody has binding specificity. The fragments can include the variable region of at least one heavy or light chain immunoglobulin polypeptide, and include, but are not limited to, Fab fragments, F(ab')$_2$ fragments, and Fv fragments.

In addition, the monospecific domains can be attached by any method known in the art to another suitable molecule. The attachment can be, for instance, chemical or by genetic engineering. The αEM10 can be produced by any recombinant means known in the art. Such recombinant antibodies include, but are not limited to, fragments produced in bacteria and non-human antibodies in which the majority of the constant regions have been replaced by human antibody constant regions. In addition, such "humanized" antibodies can be obtained by host vertebrates genetically engineered to express the recombinant antibody.

As used herein, αEM10 includes monoclonal antibody SM27-1045 or any monoclonal antibody or polyclonal antibody, that binds specifically to EM10 in such a manner as to recognize, preferentially, hematopoietic progenitor and stem cells. This also includes any αEM10 having the same antigenic specificity as SM27-1045.

The αEM10 antibodies are obtained by methods known in the art for production of antibodies or functional portions thereof. The actual methods used are described in the Examples presented herein although any method known in the art of antibody production can be used. Such methods include, but are not limited to, separating B cells with cell-surface antibodies of the desired specificity, cloning the DNA expressing the variable regions of the light and heavy chains and expressing the recombinant genes in a suitable host cell. Standard monoclonal antibody generation techniques can be used wherein the antibodies are obtained from immortalized antibody-producing hybridoma cells. These hybridomas can be produced by immunizing animals with stem cells, and fusing B lymphocytes from the immunized animals, preferably isolated from the immunized host spleen, with compatible immortalized cells, preferably a B cell myeloma.

The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P. Molecular Probes: Handbook of Fluorescent Probes and Research Chemicals (1992–1994). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazalone, and nitrophenol. The radioactive compounds that can be conjugated or incorporated into the antibodies are known to the art, and include but are not limited to technetium 99m ($^{99}$Tc) $^{125}$I and amino acids comprising any radionuclides, including, but not limited to, $^{14}$C, $^3$H and $^{35}$S.

The following examples are offered by way of illustration and not by way of limitation.

EXAMPLE 1

Cell Processing and Monoclonal Antibody Production

Cadaveric Bone Marrow and Mobilized Peripheral Blood

Cadaveric bone marrow cell suspensions derived from multi-organ donor vertebral bodies were obtained from Northwest Tissue Center (Seattle, Wash.). Patient peripheral blood samples were obtained after informed consent and chemotherapeutic regimens designed to mobilize primitive hematopoietic cells into the periphery. Multiple myeloma patients were mobilized with a high dose of cyclophosphamide and GM-CSF according to standard techniques. Non-Hodgkins lymphoma (NHL) patients were mobilized with VP16 and G-CSF.

Cells were separated over ISOPREP™, a centrifugation median (Robbins Scientific, Sunnyvale, Calif.) harvesting the low density mononuclear cells (δ<1.068 g/mL for cadaveric bone marrow, δ<1.077 g/mL for peripheral blood) and were further stained with antibodies for FACS and analysis. Production of Monoclonal Antibodies (MALs)

C57/B1 mice were tolerized to CD34$^-$ bone marrow cells by injection with cyclophosphamide (200 mg/kg) at 24 and 48 hours after interperitoneal injection with 10$^7$ CD34$^-$ bone marrow cells. After 4 weeks, this tolerization regimen was repeated. Starting approximately 1 month later, mice were immunized interperitoneally with CD34$^+$ cells (e.g. CD34$^+$ CD38$^-$ at 0.5 to 1×10$^6$ cells/mouse) at 4 week intervals for a total of three immunizations. All immunizations were in RIBI™, an adjuvant (RIBI Adjuvant Systems). Three days after the last immunization, the spleen was harvested to create hybridomas.

Splenocytes from immunized mice were fused to the myeloma partner P3xAg8.653 using standard PEG mediated fusion according to the method described by Galfre et al. (1977) Nature 266:550–552. Hybridomas from a single spleen were plated into 19×96 well tissue culture plates in RPMI+10% FCS containing HAT to kill non-hybridoma cells. Fourteen days after fusion, supernatants from the hybridoma wells containing secreted antibodies were harvested for testing.

The hybridomas secreting SM27-1045 were subcloned two to three times by limiting dilution in the presence of Hybridoma Enhancing Supplement (Sigma) to ensure monoclonality.

SM27-1045 was found to be an IgM by an ELISA in which isotype-specific alkaline-phosphatase-labeled antibodies are used to detect SM27-1045 captured in a microtiter well with immobilized anti-mouse Ig.

EXAMPLE 2

Antibody Staining, Fluorescence Activated Cell Sorting and Analysis

The buffer used in antibody staining was Dulbecco's modified phosphate buffered saline ($Ca^{++}$ and $Mg^{++}$ free) supplemented with 2% fetal bovine serum, 10 mM HEPES, 10 U/mL heparin, and 1 mg/mL human gamma globulin (GAMIMUNE™, human immune globulin, Miles, Elkhart, Ind.). Cells were incubated at $10^7$/mL in SM27-1045 hybridoma supernatant diluted ½ in buffer for 30 minutes on ice. Cells were washed and SM27-1045 binding was detected by adding PE-labelled rabbit anti-mouse IgM at 1/100 dilution (Zymed) and incubating for 30 minutes on ice. Cells were washed again and resuspended to $10^7$/mL in 2% normal mouse and 2% normal goat serum and incubated for 10 minutes on ice.

FITC or sulforhodamine-conjugated anti-CD34 antibody (Tük 3, F(ab')$_2$) was added at 3 µg/mL, and to amplify the PE signal, PE-labelled goat anti-rabbit IgC was added (Zymed, 1/100) and incubated 30 minutes on ice. Cells were washed and resuspended for cell sorting or analysis in buffer containing 1 µg/ml propidium iodide to stain non-viable cells. Cells were sorted and analyzed on a FACStar$^{PLUS}$ (Becton Dickinson, San Jose, Calif.) equipped with two lasers, one emitting at 488 nm and a second (CR-599, Coherent, Palo Alto, Calif.) tuned to 600 nm to detect sulforhodamine fluorescence.

Sort gates were established to collect cells that were sulforhodamine positive (CD34$^+$), propidium iodide$^{dim}$ (viable). These cells were further divided into subsets based upon the level of PE staining (EM10$^+$ and EM10$^-$). The sorted cells were used in the AC6.21 co-culture, methylcellulose and SCID-hu thymus assays described below.

Three color immunofluorescent labelling was performed on the FACSCAN™ (a device for immunofluorescent labeling of cells). The buffer used was Dulbecco's modified phosphate buffered saline as described above with the exception that 2% dialyzed BSA replaced the 2% FCS. Cells were stained with SM27-1045 and detected with the double layer of PE-labelled antibodies as described above. Biotinylated anti-CD38 (Leu-17, Becton Dickinson) was added at the same time as the PE-goat anti-rabbit IgG. After incubation for 30 minutes and washing, FITC-labelled anti-CD34 and streptavidin Red613 (Gibco, 1/50 dilution) were added and incubated for 30 more minutes. Cells were washed a final time and the cell pellet was resuspended in buffer containing propidium iodide. 2000 FITC positive, low SSC events (CD34$^+$ cells) were collected and displayed as FL2 (SM27-1045 or IgM isotype) versus FL3 (CD38$^+$ for moderately bright, or dead for extremely bright). The results obtained are depicted in FIG. 1 which shows that SM27-1045 binds to a substantial subset of CD34$^+$CD38$^-$ cells.

For the five color analysis cells were stained but not sorted. Cells were stained with rho123 (Molecular Probes, Eugene, Oreg.) by incubating in buffer with 1 µg/mL rho123 for 30 minutes at 37° C., washing to remove excess rho123 and then incubating cells in buffer without rho123 for 30 minutes at 37° C. to allow efflux. Subsequently, cells were stained at 4° C. with SM27-1045 or control IgM (detected with PE-labelled rabbit anti-mouse IgM, followed by PE-labelled goat anti-rabbit IgG, both from Zymed and diluted 1/100, FL2), anti-Thy-1 (GM201, detected with Texas Red-labelled goat anti-mouse IgG$_1$, FL5) and anti-CD34 (T ük 3, Cy5-labelled FL4) and propidium iodide (FL3). Rhodamine 123 staining was detected in the FL1 channel.

The results obtained in the five color assay in the five color assay are depicted in FIGS. 2A and B which shows that SM27-1045 binds to a substantial number of CD34$^+$Thy-1$^+$ cells (both rho123$^{lo}$ and rho123$^{hi}$ subsets).

The results presented in FIGS. 3A–F and 4A and B show that αEM10 subdivides CD34$^+$ cells; αEM10 binds approximately 60% of CD34$^+$ cells from bone marrow and 1–2% of a mononuclear cells on average and binds nearly all CD34$^+$ Thy-1$^+$. The results further indicate that SM27-1045 does not bind significant numbers of CD34$^-$ cells.

EXAMPLE 3

Staining of Mobilized Peripheral Blood

Mobilized peripheral blood was obtained from a non-Hodgkins lymphoma (NHL) patient and a multiple myeloma patient and processed as described in Example 1. Cells were then stained with the antibodies indicated in FIGS. 5A and B and 6A–D according to the method described in Example 2.

Figure 5A:
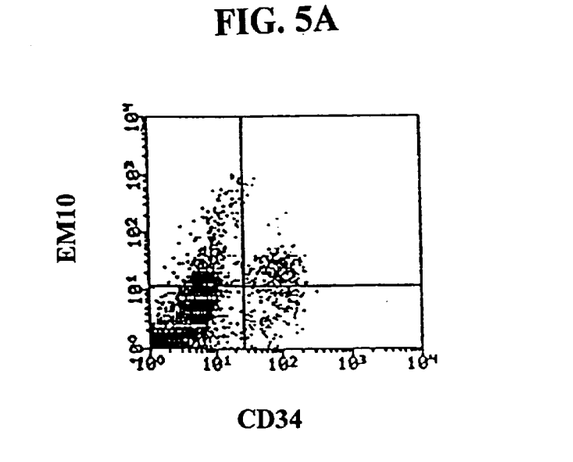
FIGS. 5A and B depicts the FACS analyses of cells obtained from mobilized peripheral blood stained with antibodies to CD34 and EM10 (FIG. 5A) or isotype control antibody (FIG. 5B).
Figure 5B:
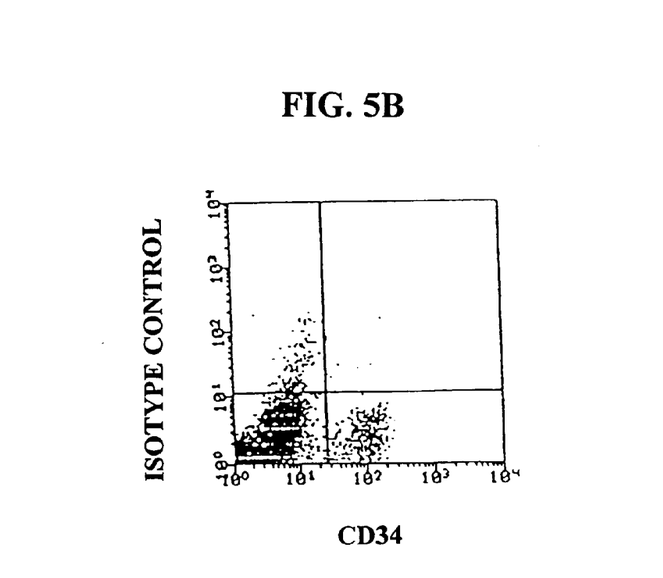
Figure 6A:
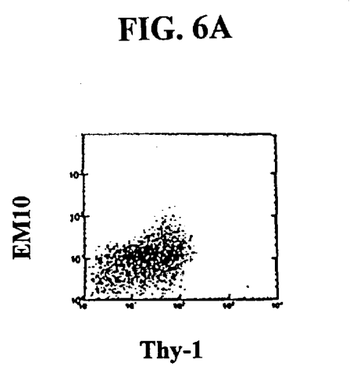
FIGS. 6A–D depicts the FACS analyses of mobilized peripheral blood cells of CD34 gated (FIGS. 6A and 6C) and ungated (FIGS. 6B and 6D) cells.
Figure 6B:
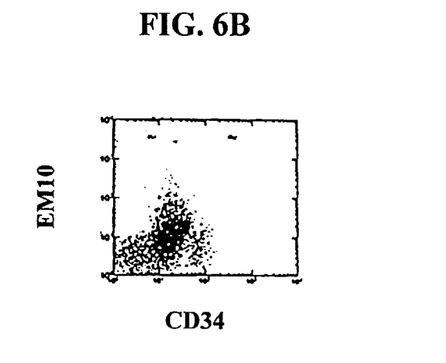
Figure 6C:
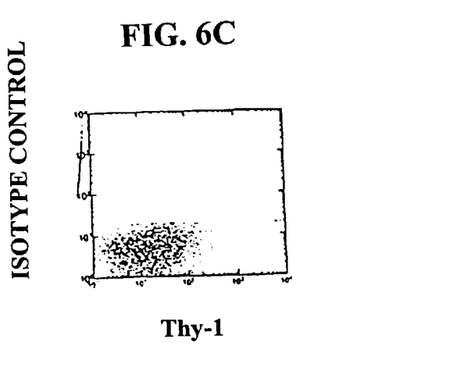
Figure 6D:
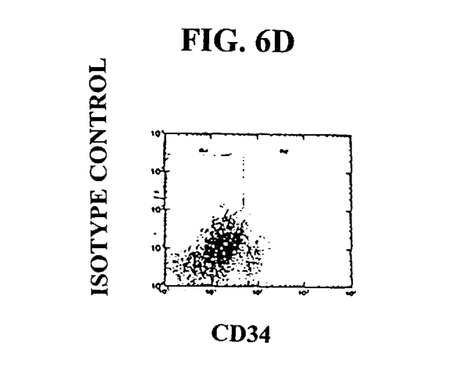

The results depicted in FIGS. 5A and B show binding of SM27-1045 to mobilized peripheral blood CD34$^+$ cells is similar to that observed in bone marrow. αEM10 binds 2–90% (avg. 39%, n=10) CD34$^+$ cells from mobilized peripheral blood. Five of the 10 samples had less than 20% of CD34$^+$ cells bound by SM27-1045. It appears that EM10 is more variably expressed in mobilized peripheral blood than in bone marrow. These findings are similar to the results obtained with mAbs to c-kit. It is unlikely that αEM10 binds to c-kit based on the cell line staining data shown in Table 3. It can be the case that the antigen bound by EM10 is involved in the process of stem/progenitor cell mobilization, such as has been proposed for c-kit. FIGS. 6A–D shows that αEM10 binds a subset of CD34$^+$Thy-1$^+$ cells from mobilized peripheral blood.

EXAMPLE 4

Immunofluorescence Staining of Various Cell Lines by αEM10

The expression of EM10 on a variety of cultured hematopoietic cell lines was tested by indirect immunofluorescence. All cultured cell lines were obtained from the ATCC. Human umbilical vascular endothelial cells (HUVEC) Was obtained from Cell Systems, Kirkland, Wash. Cell lines were immunolabelled with SM27-1045 at 4° C. for 30 minutes, washed and further incubated for 30 minutes and detected using PE-labelled rabbit anti-mouse IgM (Zymed). After washing twice the cells were subjected to flow cytometric analysis using a FACScan. Analysis gates were set according to a non-binding isotype matched IgM control antibody.

For determination of neuraminidase sensitivity of the epitopes, HEL or bone marrow cells were incubated at $10^7$ cells/mL with 0 to 500 mU/mL of neuraminidase for 1 hour at 37° C. In order to determine the glycoprotease sensitivity of the epitopes, cells were incubated at $10^7$ cells/mL in HBSS and a 1/10 dilution of O-sialoglycoprotein endopeptidase (CLE100, Accurate Chemical). Cells were incubated at 37° C for 30 minutes. Cells were then washed and subsequently tested for antibody binding by indirect immunofluorescence. The results obtained are presented in Table 3 which shows the percent of EM10 positive cells for each cell line tested.

Figure 7A:
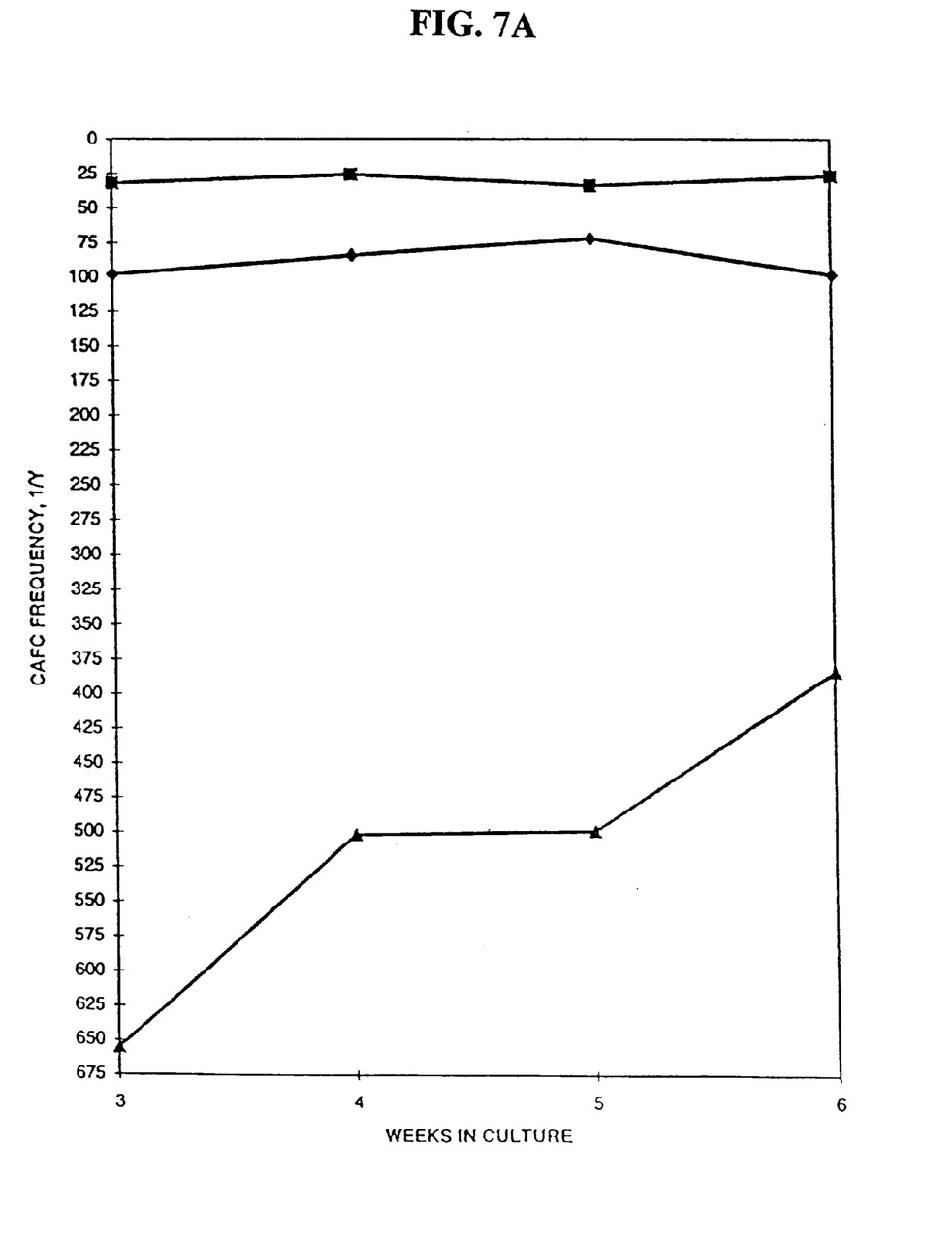
FIG. 7A depicts the results obtained from the first coculture and FIG. 7B depicts the results obtained from the second coculture.
Figure 7B:
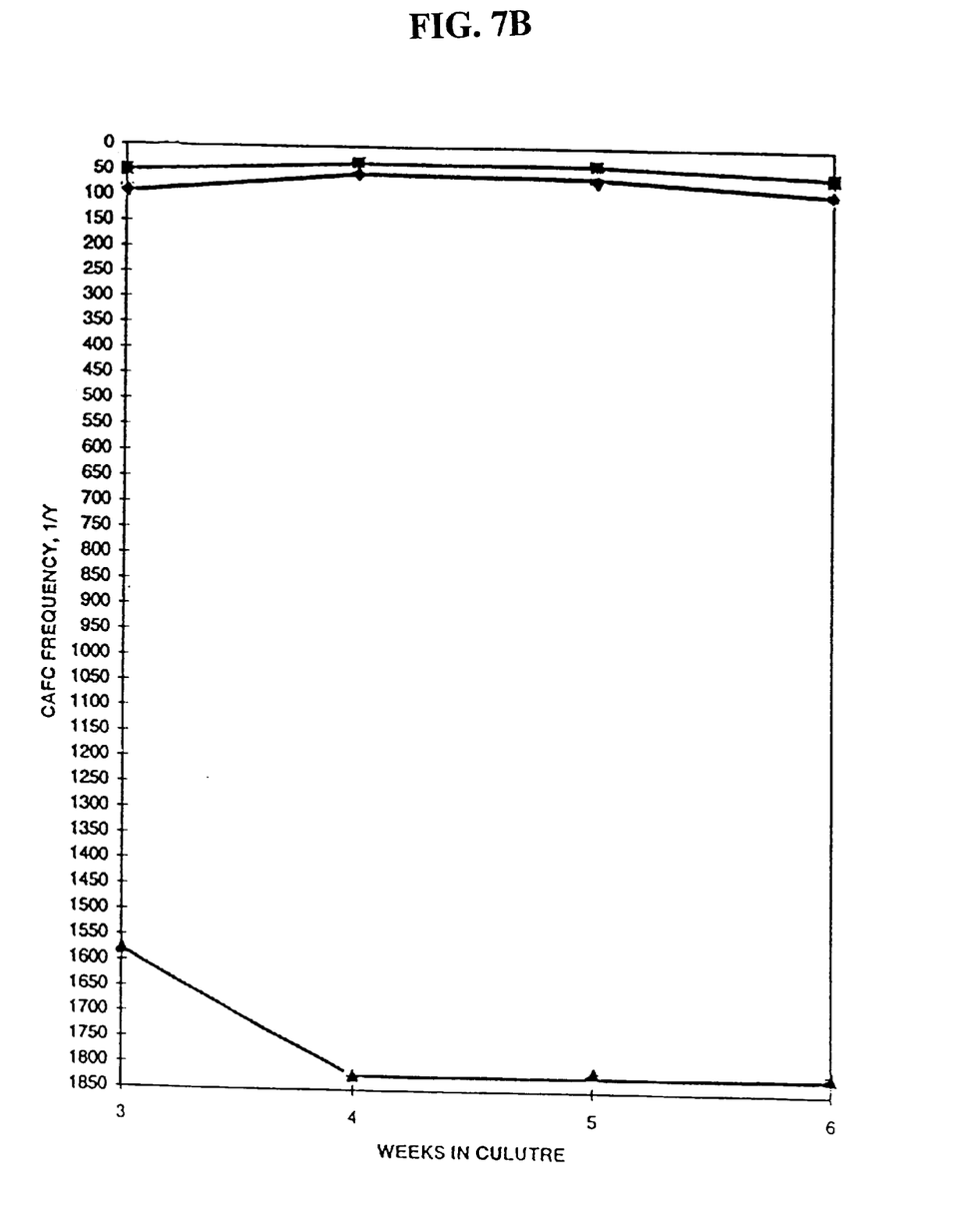
Figure 8A:
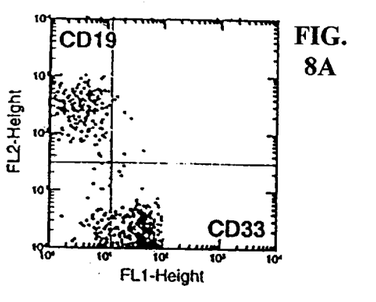
FIGS. 8A–P depicts the phenotypic analyses of progeny from CD34⁺EM10⁺ (FIGS. 8A–8H) or CD34⁺ (FIGS. 8I–8P) cells plated at limiting dilution and grown in SyS1 co-culture for 6 weeks.
Figure 8B:
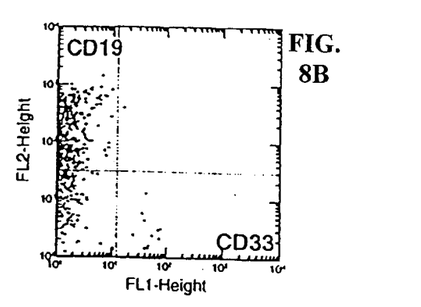
Figure 8C:
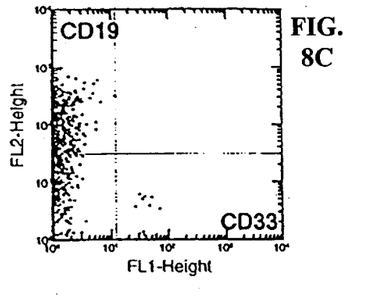
Figure 8D:
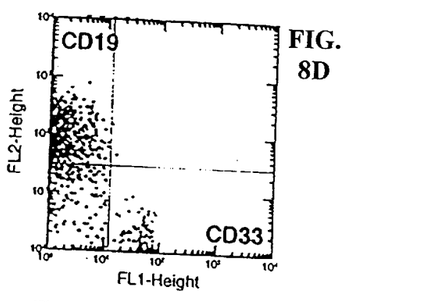
Figure 8E:
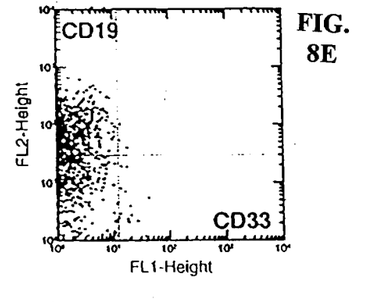
Figure 8F:
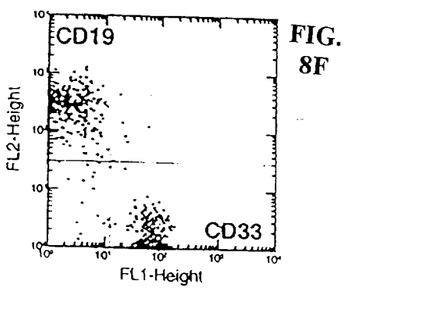
Figure 8G:
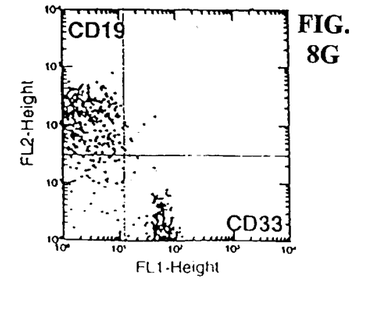
Figure 8H:
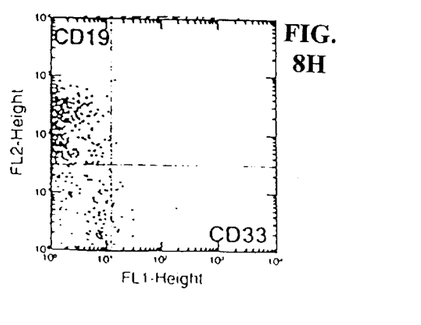
Figure 8I:
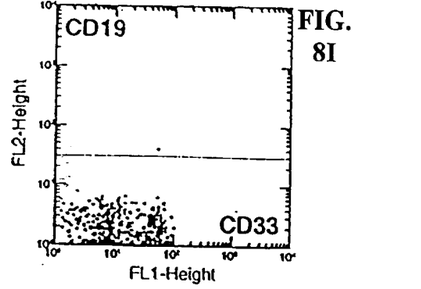
Figure 8J:
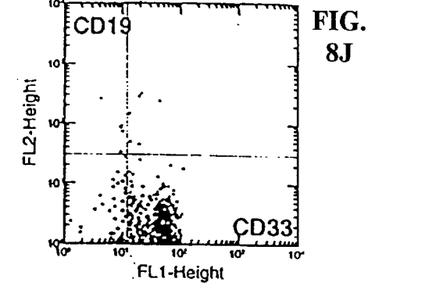
Figure 8K:
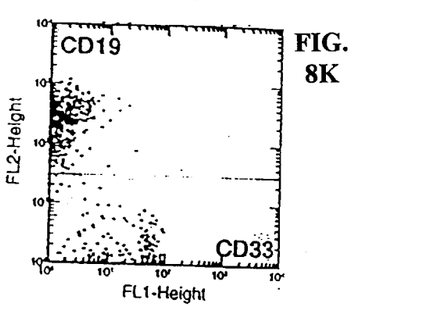
Figure 8L:
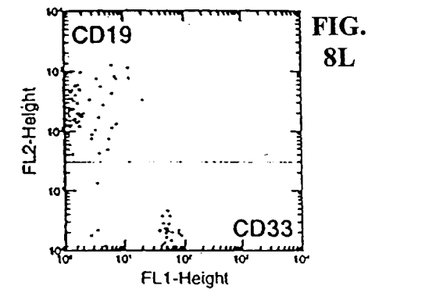
Figure 8M:
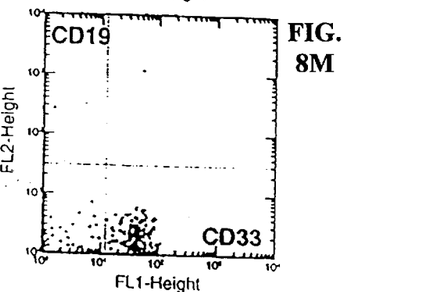
Figure 8N:
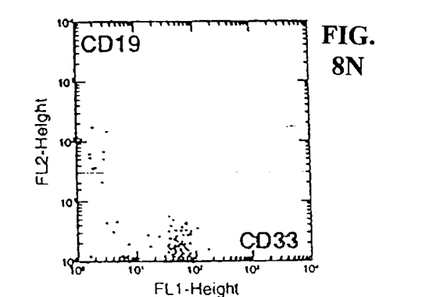
Figure 8O:
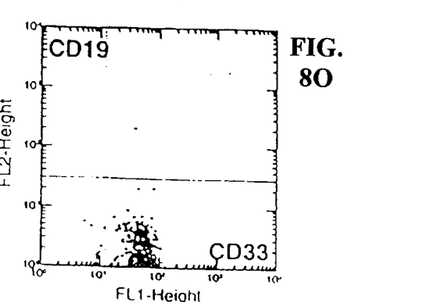
Figure 8P:
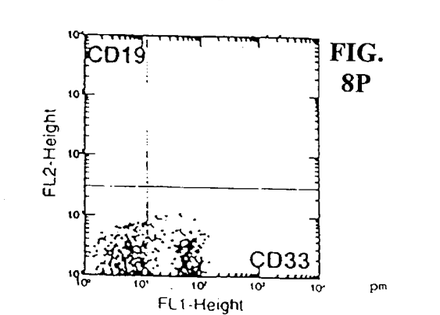

Peripheral blood mononuclear cells (PBL) and HUVEC were also tested for the expression of epitopes bound by αEM10. As a comparison, the HUVEC were first incubated with IL-1β at 10 ng/ml for 4 hrs. IL-1β activates some integrins on endothelial cells. The results are presented in Table 3. The pattern of reactivity is not identified as similar to that described for mAbs to other antigens which have been described as expressed on $CD34^+$ cells. Furthermore, no binding to PBL was observed. The level of epitope expression is modest on both bone marrow and other positively stained cells tested. The treatment of bone marrow cells with neuraminidase or glycoprotease does not diminish the binding of SM27-1045 indicating that carbohydrate components are unlikely to be major aspects of the epitope defined by this mAb. The staining of HUVEC after activation with IL-1β is no different from untreated cells.

obtained from 2 separate sets of experiments are depicted in Table 4 and FIGS. 7A and 7B. The results show that the long term CAFC is enriched 15–50 fold in the double positive subset of $CD34^+$ cells compared to the single positive subset ($CD34^+EM10^-$). Phenotypic analyses showed $CD34^+$ $EM10^+$ cells were able to produce both lymphoid and myeloid cells in the SySi co-culture assay (FIG. 8).

Methylcellulose Assay

Sorted cell populations were plated into methylcellulose cultures to determine colony forming cell activity according to the method described by Brandt et al. (1992) Blood 79:634. Growth factors were kit ligand (100 ng/mL), erythropoletin (2 U/mL), GM-CSF (10 ng/mL) and IL-3 ng/mL). The results in Table 4 show that αEM10 binds about 80% of the CFU-GM and CFU-Mix and ⅔ of BFU-E.

SCID-hu Thymus Assay

TABLE 3

| KG1a | KG1 | Jurkat | N417 | HEL | HEL$^+$ neuraminidase | Daudi | Molt4 | HL60 | K562 | U937 | TFI | MCF7 | T47D | HUVEC | HUVEC$^+$ IL-1(4h) | PBL (ficolled) |
|---|---|---|---|---|---|---|---|---|---|---|---|---|---|---|---|---|
| n = 3 | | n = 2 | n = 4 | n = 4 | | | | | n = 2 | | n = 3 | n = 2 | n = 2 | n = 2 | | n = 6 |
| <5 | <5 | <5 | 70 | 10 | 16 | <5 | <5 | <5 | <5 | <5 | 38 | <5 | <5 | <5 | <5 | <3 |

EXAMPLE 5

Characterization of EM10$^+$ Cells

Co-culture

Sorted cell populations were analyzed by limiting dilution analysis for cobblestone area forming cell frequency AC6.21 by limiting dilution analysis according to the method described by Baum et al. (1989).

Briefly, $CD34^+$ cadaveric bone marrow cells sorted into $CD34^+$ $EM10^+$ and $CD34^+$ $EM10^-$ subsets as described in Example 1. A passage of AC6, (Whitlock et al. (1987) Cell 48:1009–1021), AC6.21, was used herein and is alternatively referred to as SyS1. Confluent AC6.21 stromal cell layers were maintained for 3–7 weeks without passage by changing of the tissue culture medium every 5–7 days. The culture was with the addition of human recombinant IL-6 (10 ng/mL) and LIF (20 ng/mL) to enhance the proliferation of adult bone marrow cells. The ability to give rise to both myeloid and B lymphoid progeny was determined after 6 weeks of coculture by staining with anti-CD19-FITC, and anti-CD15-FITC and anti-CD33-PE (all from Becton Dickinson) and analyzing on the FACSCAN. The results Sorted cell populations were microinjected into depleted fetal thymic pieces and implanted under the kidney capsule of SCID-hu mice according to the method described by Galy et al. (1994) Blood 84:104–110. Six weeks after implantation, thymic pieces were recovered and analyzed for the presence of T cell progeny. Preliminary SCID-hu thymus assays do not establish whether all T cell progenitors are bound by this mAb. The results obtained are depicted in Table 4. The results obtained indicate that αEM10 subdivides T cell progenitor activity as determined by the SCID-hu thymus assay which reads out both stem cell and lymphoid progenitor potential.

TABLE 4

Functional Readouts of Cell Populations Subsetted With σSM27-1045

| Tissue | Sort Purity (Cross-contamination) | % Double Positive | Population Assayed | AC6.21 Results Week 5 | CFC/10$^5$ cells BFU-E/CFU-GM/CFU-Mix | SCID-hu thymus results |
|---|---|---|---|---|---|---|
| 10362 | 1–3% | 62 | CD34$^+$ EM10$^+$ | 1/34 | 11125/5200/875 | 1/1 |
| | | | CD34$^+$ EM10$^-$ | 1/499 | 6450/600/150 | 1/1 |
| | | | CD34$^+$ | 1/72 | 4150/1925/275 | 4/4 |
| 9041 | <1% | 79 | CD34$^+$ EM10$^+$ | 1/35 | 1600/225/74 | |
| | | | CD34$^+$ EM10$^-$ | 1/1822 | 800/25/0 | |
| | | | CD34$^+$ | 1/60 | 7350/1125/175 | |

Although the foregoing invention has been described in some detail by way of illustration and example for purposes of clarity of understanding, it will be apparent to those skilled in the art that certain changes and modifications can be practiced. Therefore, the description and examples should not be construed as limiting the scope of the invention, which is delineated by the appended claims.

What is claimed is:

1. A method of determining the stem cell content in a sample of hematopoietic cells comprising the steps of:
   (a) combining a mixture of hematopoietic cells with an antibody that recognizes and binds to EM10 under conditions which allow the antibody to specifically bind to EM10; and
   (b) quantitating the cells recognized by the antibody wherein EM10 is a cell surface marker recognized and bound by an antibody having the same antigen specificity as the antibody produced by the hybridoma having accession number ATCC HB 11917.

2. The method according to claim 1, further comprising the step of selecting the cells for expression of at least one additional marker associated with stem cells.

3. The method according to claim 2 wherein the additional marker is selected from the group consisting of $CD34^+$, $Thy-1^+$, $P-gp^+$ and $c-kit^+$.

4. The method according to claim 1 further comprising the step of selecting the cells for lack of expression of at least one lineage specific ($LIN^-$) marker.

5. The method according to claim 4 wherein the lineage specific marker is selected from the group consisting of CD14, CD15, CD38, HLA-DR, CD71 and CD33.

6. The method according to claim 4 wherein the lineage specific marker is selected from the group consisting of CD2, CD16, CD19, CD20 and glycophorin A.

* * * * *